United States Patent [19]
Joyce

[11] Patent Number: 5,807,717
[45] Date of Patent: Sep. 15, 1998

[54] COUPLED ISOTHERMAL POLYNUCLEOTIDE AMPLIFICATION AND TRANSLATION SYSTEM

[75] Inventor: Gerald F. Joyce, Encinitas, Calif.

[73] Assignee: The Scripps Research Institute, La Jolla, Calif.

[21] Appl. No.: 231,587

[22] Filed: Apr. 20, 1994

Related U.S. Application Data

[63] Continuation of Ser. No. 939,302, Sep. 2, 1992, abandoned.
[51] Int. Cl.[6] .............................. C12P 19/34; C12Q 1/68
[52] U.S. Cl. ............................................ 435/91.1; 435/6
[58] Field of Search ............................ 435/6, 68.1, 91.2, 435/91.1

[56] References Cited

U.S. PATENT DOCUMENTS 5,324,637   6/1994   Thompson et al. .................... 435/68.1

FOREIGN PATENT DOCUMENTS 9105058   of 1991   WIPO .............................. C12Q 1/68

OTHER PUBLICATIONS

Spirin, Alexander S., et al., A Continuous Cell–Free Translation System . . . Science, vol. 242, pp. 1162–1164.
L. A. Ryabova, et al., Preparative Synthesis of Globin in a Continuous . . . Nucleic Acids Research; vol. 17, No. 11, 1989; p. 4412.
Vladimir I. Baranov, et al.,; Gene Expression in a Cell–free System . . . Gene, 84, 1989; pp. 463–466.
Suresh I. S. Rattan; Continuous Gene Expression in vitro the Spirin System; Tibtech, Oct. 1990, vol. 8, pp. 275–276.
P. A. Krieg, et al., Functional Messenger RNAs are Produced by SP6 . . . Nucleic Acids Research, vol. 12, No. 18, 1984; p. 7057–7070.
David A. Nielsen, et al.,; Preparation of Capped RNA Transcripts . . . Nucleic Acids Research, vol. 14, No. 14, 1986, pp. 5936.
Bryan E. Roberts, et al., Efficient Translation of Tobacco Mosaic Virus . . . Proc. Nat. Acad. Sci. USA, vol. 70, No. 8, p. 2330–2334, Aug. 1973.
Geoffrey Zubay, In Vitro Synthesis of Protein in Microbial Systems; pp. 267–287.
Hugh R. B. Pelham, et al., An Efficient mRNA–Dependent Translation . . . Eur. J. Biochem, 67, 247–256, 1976.
William C. Merrick, Monitoring Cloned Gene Expression; Translation of Exogenous mRNAs in Reticulocyte Lysates, pp. 606–615.
Translation in vitro; pp. 115–132.
J. Cell Biology 108:229–241 (Feb. 19189) Kozak, M. "Scanning Model for Translation: An Update".
P.N.A.S. 77:7029–7033 (Dec. 1980) Yang, H–L, et al "Cell–Free Coupled Transcription–Translation . . . ".
J. Bacteriology 156:1359–1362 (Dec. 1983) Bassett, C.L. et al "In Vitro Coupled Transcription–Translation . . . ".
205 U.S.P.Q. 1069 (CCPA 1980) In re Kerkhoven.
Kigawa et al J. Biochem 110:166–168 (1991).

*Primary Examiner*—W. Gary Jones
*Assistant Examiner*—Eggerton Campbell
*Attorney, Agent, or Firm*—Fish & Richardson P.C.

[57] ABSTRACT

A cell-free system for polynucleotide amplification and translation is disclosed. Also disclosed are methods for using the system and a composition which allows the various components of the system to function under a common set of reaction conditions.

19 Claims, 1 Drawing Sheet

COUPLED ISOTHERMAL POLYNUCLEOTIDE AMPLIFICATION AND TRANSLATION SYSTEM

This is a continuation of application Ser. No. 07/939,302 filed on Sep. 2, 1994, now abandoned.

This invention was made with Government support under Grant No. NASA Grant #NAGW-2881 awarded by the National Aeronautics and Space Administraton. The Government has certain rights in this invention.

BACKGROUND

1. Field of the Invention

This invention relates generally to the transcription, amplification and translation of nucleotides. Specifically, the invention relates to a system whereby polynucleotide amplification and in vitro translation occur spontaneously under the same reaction conditions.

2. Description of Related Art

Expression of foreign genes in living cells is often subject to a number of limitations. A major limitation on in vivo production of polypeptides is where the polypeptide is unstable or, in some cases, toxic to the cell. For example, various proteases, immunotoxins, or lectins cannot be safely produced using such in vivo systems.

In light of the significant drawbacks associated with in vivo polypeptide expression, there has been considerable interest in developing in vitro expression systems. However, a major limitation with the cell-free translation systems described to date is the low yield of the polypeptide product produced. This low yield may be due to factors such as the lability and short half-life of mRNA in these systems. Typically only two to three polypeptide chains are produced for each mRNA chain used in such systems. One way to compensate for this low yield is to use large amounts of pre-synthesized mRNA, although the supply of mRNA is soon expended such that more pre-synthesized mRNA must be supplied to maintain production of polypeptide.

Several continuous cell-free translation systems theoretically capable of producing polypeptides in high yield have been developed (Spirin, et al., Science, 242:1162, 1988; Ryabova, et al., Nucl. Acids Res., 17:4412, 1989). These systems prolong the functioning of a cell-free translation system. However, the reaction products, including synthesized polypeptides, must be continuously removed from the reaction mixture, and the initial concentrations of low molecular weight substrates must be continuously restored. In addition, although continuous cell-free translation systems produce high yields of synthesized protein, these systems have the disadvantage of doing so only over long periods of time. Typically, these systems require 10 to 100 hours to produce larger quantities of protein. Existing in vitro translation systems have the further disadvantage of requiring prior synthesis of large amounts of mRNA using either T7 or SP6 polymerases. This can be costly and introduce extra steps into the protocol.

More recently, coupled transcription-translation systems have been studied which retain the advantages of a cell-free translation system and use DNA molecules directly as templates for transcription and subsequent translation. However, this coupled system still requires the cloning of cDNA or genomic DNA lacking introns into an expression vector containing the T7 or SP6 promoter, for example. As a result, it is usually necessary to modify the initial cDNA or genomic clone to optimize the length of the 5' or 3' untranslated sequence adjacent to the protein coding region in order to increase translation efficiency. Typically, such modification adds several days to the protocol.

A more desirable system which would greatly reduce the time period for production of significant amounts of protein would include the ability to continuously amplify the mRNA template, the DNA template, and synthesize protein in a single system. In so doing, the amount of both the mRNA transcripts and the DNA from which the mRNA transcripts are transcribed would increase, thereby continually increasing the yield of protein.

In vitro, the synthesis of double-stranded DNA from mRNA, the synthesis of mRNA from DNA, and the translation of mRNA into protein proceed by different mechanisms, utilizing different enzymes and different reaction conditions (e.g., buffers, temperature, time periods, cofactors). To date, reaction conditions which allow translation of mRNA and those which allow polynucleotide amplification have been incompatible. Therefore, although it would be highly desirable, it would be unexpected to successfully devise a single unified system whereby RNA amplification and in vitro translation could proceed under a single set of reaction conditions without the continuous input of new complex components, such as polynucleotide, or the removal of product. The present invention solves the problems of the prior art by providing a novel system wherein the reaction conditions are compatible with isothermal RNA amplification and in vitro translation proceeding simultaneously.

SUMMARY OF THE INVENTION

The present invention provides a novel cell-free system whereby polynucleotide amplification and in vitro translation proceed simultaneously under a common set of reaction conditions. Prior to the development of the invention, such a unified coupled system did not exist and was not thought possible because synthesis of mRNA to DNA, transcription of mRNA from DNA, and translation of mRNA into protein, occur under such distinct, and typically mutually hostile, conditions. Factors such as differences in temperature, buffers, and enzymes previously had made the utilization of a single, unified, simultaneous reaction system for polynucleotide amplification and translation unattainable. Consequently, it was heretofore extremely time-consuming to synthesize large quantities of protein for commercial and other purposes.

The invention addresses the failings of the prior art by providing a unified system which allows the necessary biosynthetic reactions to take place quickly and efficiently in a single vessel at a constant temperature. Also included is a buffer composition which allows the system to proceed at a high level of efficiency.

DETAILED DESCRIPTION

Figure 1:
FIG. 1 shows isothermal amplification of RNA in the presence of varying concentrations of $MgCl_2$ in the coupled system. [$\alpha$-$^{32}$P]-GTP was included to show incorporation into newly synthesized RNA.

The present invention provides a cell-free system for polynucleotide amplification and in vitro translation where the components of the system function under a common set of reaction conditions. The system includes an RNA-dependent DNA polymerase, a polynucleotide primer which allows the RNA-dependent DNA polymerase to function, a DNA-dependent RNA polymerase, a polynucleotide primer which allows the DNA-dependent RNA polymerase to function, deoxyribonucleotide triphosphate, ribonucleoside triphosphate and a cell-free in vitro translation composition. The coupled isothermal polynucleotide amplification and in vitro translation system of the invention is a unified system which does not require temperature cycling or similar complex manipulation. The invention also provides a buffer solution which is used in conjunction with the cell-free system to achieve efficient in vitro transcription, amplification and in vitro translation.

The ability to produce substantial quantities of protein by in vitro DNA synthesis and transcription has several important applications. It allows production of proteins that would be toxic or unstable in vivo. It also allows incorporation of non-standard amino acids into protein via addition of appropriate tRNAs to the reaction milieu. In vitro production of combinatorial libraries of polypeptides based on translation of a mixed population of synthetic mRNAs can also be achieved.

The term "cell-free system" refers to a preparation of a non-living extract for use in amplification of polynucleotides and translation in vitro. The cell-free system contains all factors required for the translation of mRNA, for example ribosomes, tRNAs, aminoacyl synthetases, elongation factors and initiation factors. Typically, exogenous mRNA of interest is added to the cell-free system to initiate the amplification cycle, although DNA, such as cDNA, can also be used. Cell-free systems known in the art, such as wheat germ (Roberts, et al., *Proc.Natl.Acad.Sci. USA*, 70:2330, 1973) or reticulocyte (Pelham, et al., *Eur. J. Biochem.*, 67:247, 1976) extracts can be made devoid of active endogenous mRNA by treatment with micrococcal nuclease and, therefore, provide a system whereby only the input mRNA of interest is translated.

"Polynucleotide amplification" refers to the continuous cycle of single-stranded DNA synthesis from mRNA, second strand complementary DNA synthesis, and transcription of mRNA from the template DNA. In the present invention, reaction products are amplified every time the cycle proceeds. A polynucleotide refers to a polymer of deoxyribonucleotides or ribonucleosides.

"RNA-dependent DNA polymerase" denotes an enzyme which is capable of synthesizing DNA from an RNA template, such as reverse transcriptase (RT). RT is derived from retroviruses and is used to make DNA copies of RNA. RT first synthesizes a single-stranded DNA copy of the mRNA (cDNA) and then incorporates nucleotides to synthesize the second complementary strand of DNA. RTs of the invention include but are not limited to Moloney murine leukemia virus (MOMLV) RT and Avian myeloblastosis virus (AMV) RT. Preferably, MoMLV RT is utilized. RT may also contains a DNA-directed DNA polymerase activity and RNase H activity which degrades RNA in an RNA:DNA hybrid. Other known enzymes which possess the activities inherent to a RNA-dependent DNA polymerase are included in the invention.

As used herein, a "polynucleotide primer which allows the RNA-dependent DNA polymerase to function" refers to a oligodeoxynucleotide which allows extension of the DNA being synthesized by the RNA-dependent DNA polymerase from an RNA template. The DNA synthesized by RT from the RNA template is called complementary DNA (cDNA). The term "primer" as used herein refers to a sequence comprising two or more deoxyribonucleotides or ribonucleotides, preferably at least eight, which sequence is capable of initiating synthesis of an extension product, and which is substantially complementary to a target nucleic acid strand. The primer typically contains 15–22 or more nucleotides, although it may contain fewer nucleotides. Examples of such oligodeoxynucleotide primers of the invention include, but are not limited to, an oligo (dT) polymer, a collection of random DNA sequences, or a specific sequence. An oligo (dT) polymer can be used to prime the cDNA synthesis from the poly A tail of any mRNA having a poly A region. If the sequence of the mRNA is unknown, or if it is desirable to account for degeneracy in the mRNA sequence, a collection of random DNA sequences can alternatively be used. Further, if the sequence of the mRNA which is to be amplified and translated is known, a specific sequence primer can be utilized to allow initiation of cDNA synthesis from that specific sequence on the mRNA. Preferably the primer which allows RT to function is complementary to sequences at the 3'-terminal region of the mRNA, although the invention also includes primers which extend into the non-translated portion of the mRNA.

"DNA-dependent RNA polymerase" as used herein, refers to an enzyme which synthesizes mRNA transcripts from DNA. DNA-dependent RNA polymerases used in the invention include but are not limited to *E. coli* RNA polymerase and bacteriophage RNA polymerase. The preferred polymerase of the invention is derived from the class of bacteriophage RNA polymerases which are encoded by members of a related family of bacteriophages which includes T7, T3, and SP6. Each RNA polymerase is a single subunit enzyme that recognizes a specific promoter sequence. Each RNA polymerase initiates transcription specifically and exclusively from its own promoter sequence. The preferred RNA polymerase of the invention is the T7 polymerase.

As used herein, the "polynucleotide primer which allows the DNA-dependent RNA polymerase to function" refers to a oligodeoxynucleotide sequence which contains nucleotides complementary to a single-stranded DNA (synthesized from mRNA by RT, for example) and contains a sequence which is recognized by a DNA-dependent RNA polymerase. Preferably, the primer of this invention contains a specific sequence for the second-strand of DNA to be synthesized, adjacent to nucleotides which encode a DNA-dependent RNA polymerase promoter region. For example, the preferred RNA polymerase of the invention is T7 polymerase and, therefore, the corresponding primer would contain sequences for the T7 promoter region. Thus, the newly synthesized double-stranded DNA molecule contains a T7 promoter and can be efficiently transcribed to the corresponding mRNA by T7 RNA polymerase. Oligodeoxynucleotide primers which allow the DNA dependent RNA polymerase to function are most preferably complementary to the 3'-terminal region of the single-stranded cDNA. Therefore, the newly synthesized second strand of DNA would contain the T7 promoter sequence at the 5'-terminal region.

The primers which allow the DNA-dependent RNA polymerase to function can be a collection of random primers rather than one specific sequence. A specific species of mRNA of interest can be included in the reaction mixture and, by designing primers which selectively bind to that particular mRNA, larger quantities of the desired protein can be produced. For example, if a small amount of protein is isolated, it can be microsequenced by methods known in the art. From this sequence, primers can be designed that will select the desired mRNA for amplification and translation in the system of the invention. To account for degeneracy, in that more than one codon can code for a particular amino acid, an appropriate collection of primers should be used. Alternatively, if the class of proteins, for example kinases, is known, and a consensus sequence within the mRNA is known for that class, specific primers can be designed to select only mRNAs in that class.

Oligodeoxynucleotide primers of the invention are chemically synthesized by any of the methods in the art. The oligodeoxynucleotides are most advantageously prepared by utilizing any of the commercially available, automated nucleic acid synthesizers. Conventional phosphotriester (Edge, et al., *Nature,* 292:756, 1981), phosphodiester or phosphoramidite (Beaucage, et al., *Tet Letts,* 22:1859 1981) methods can be used to prepare synthetic oligodeoxynucleotide primers. While any length oligonucleotide may be utilized in the practice of the invention, sequences shorter than 2 bases may be less specific in hybridizing to the target mRNA. Hence, hybridizing oligonucleotides having 15 or more nucleotides are preferred. Sequences longer that 30 nucleotides may also be somewhat less effective in binding specifically to the target mRNA. Thus, hybridizing oligomers of 15–20 nucleotides are most preferred in the practice of the present invention. The exact length of the primer depends on many factors, including temperature, buffer, and nucleotide composition but can be determined by routine experimentation.

Primers used according to the method of the invention are designed to be "substantially" complementary to each strand of nucleotide sequence to be amplified. Substantially complementary means that the primers must be sufficiently complementary to hybridize with their respective strands under conditions which allow the agent for polymerization to function. Preferably, the terminus of the primer that is extended has perfectly base paired complementarity with the complementary flanking strand.

The deoxyribonucleotide (dNTP) and ribonucleoside (rNTP) triphosphate of the invention include ATP, GTP, TTP (UTP for ribonucleoside), and CTP. These are included in the cell-free system for incorporation by the DNA and RNA polymerases into DNA and RNA respectively. It may also be desirable for the RNA synthesized to contain a 5'-capped structure to increase the efficiency of in vitro translation, therefore, diguanosine GTP ((G-5'ppp5'-G) TP) can also be included in the reaction.

The "cell-free in vitro translation composition" of the invention refers to a preparation of cell extract which allows mRNA to be synthesized into protein. The extract contains all of the factors required for protein synthesis from mRNA. The cell-free in vitro translation composition which can be incorporated into the cell-free system must be capable of functioning (i.e., allowing translation to occur) under conditions which also allow polynucleotide amplification to occur. Thus, it is possible to identify acceptable cell-free in vitro translation compositions by placing the composition in the cell-free system disclosed herein and measuring, for example, the production of protein from amplified polynucleotide.

The cell-free in vitro translation composition of the invention includes but is not limited to a composition derived from archaebacterial cells, eubacterial cells, and eukaryotic cells, including plant cells. Archaebacterial cells of the invention include species of Sulfolobus, Thermoproteus, Halobacterium, Methanospirillum, Methanobacterium and Methanococcus, for example. Eubacterial cells of the invention include true bacteria of the gram positive and gram negative classes, such as species of Flavobacterium, Pseudomonas, Escherichia, Agrobacterium, Bacillus, and Anacystis. Preferably the eubacterial cell of the invention is gram negative and, more specifically, is *Escherichia coli.*

The cell-free in vitro translation composition of the invention can also be derived from a eukaryotic cell. Eukaryotic cell-free compositions known in the art translate mRNAs from viral or eukaryotic origin efficiently. Examples of such systems include those derived from animal cells such as Krebs II ascites tumor, rat and mouse liver, Hela cells, mouse L cells, Chinese hamster ovary (CHO) cells, and reticulocytes. Preferably the in vitro translation composition of the invention is derived from a eukaryote, specifically, an animal cell. More specifically, the system is derived from a rabbit reticulocyte. The rabbit reticulocyte lysate from Promega Biotec (TNT, Madison, Wis.) has been found to be particularly useful and is preferred according to the invention.

The cell-free in vitro composition of the invention also includes a composition derived from a plant cell. Examples of such compositions include but are not limited to wheat cells, and in particular wheat germ, and rye embryo. Preferably the plant cell-derived composition is from a wheat cell.

The cell-free system of the invention contains components which function under a common set of reaction conditions. This refers to the ability of cell-free polynucleotide (DNA and RNA) amplification and in vitro translation to operate in the same buffer, at a constant temperature, and for the same period of time. These conditions allow the DNA template and corresponding mRNA to be continually amplified in the same reaction that allows the mRNA to be translated into protein. In contrast to the known continuous transcription-in vitro translation systems, the present invention offers the advantage of the production of large quantities of protein in a short period of time, without the need for continually manipulating the system, for example, by the addition of complex components such as in mRNA and cDNA.

The "solution useful for the operation of the cell-free system" refers to the composition which allows polynucleotide amplification and in vitro translation to occur consecutively, without a change in reaction conditions. The solution contains a biological buffer such as MES, Bis-Tris, Pipes, MOPSO, HEPES, EPPS, and Tris (hydroxymethyl) aminomethane salts, for example. The preferred buffer of the invention is a Tris salt, specifically, Tris-HCl. The solution of the invention also includes a magnesium source. The magnesium source of the invention includes but is not limited to magnesium chloride and magnesium acetate. Preferably, the magnesium of the invention is magnesium chloride ($MgCl_2$). The solution also includes both deoxyribonucleotide and ribonucleoside triphosphates as described above, as substrate for the polymerase incorporation into DNA and RNA, respectively. Also included is a mixture of all 20 amino acids which are incorporated into protein during in vitro translation of the mRNA.

The biological buffer of the invention is present in a concentration of from about 10 mM to about 100 mM and at pH from about 7.2 to about 8.2, most preferably 40 mM and pH 7.5. The rNTPs of the invention are present from about 1 to about 4 mM each, preferably 2.4 mM. The dNTPs are present at a concentration of about 0.05 to about 0.5 mM each, and most preferably at about 0.2 mM. The amino acids of the solution are present at a concentration of about 0.5 to about 2 mM and most preferably at 1 mM. The $MgCl_2$ is present at about 5.0 to about 10.0 mM, and most preferably at 7.5 mM. The reaction of amplification and translation occurs at a temperature of about 35°–40° C. and most preferably at 37° C. For example, lower temperature may be more desirable for primers with a high A-T base composition. The time period of the reaction is from about 1 to about 4 hours, preferably 2 hours. Those of skill in the art will realize that those conditions can be modified appropriately depending on particular need in order to achieve a cell-free polynucleotide amplification and translation system of the invention.

In addition to the solution of the invention, the other components of the cell-free polynucleotide amplification and translation system are present in the following amounts: (1) input RNA of interest is added at a final concentration from about $10^{-5}$ to $10^2$ nM, most preferably 1.0 nM. The concentration of message is adjusted to achieve maximum incorporation of amino acid into protein and may vary within the given concentrations depending on the particular message. It is a matter of routine to establish the optimal RNA concentration for each mRNA species. (2) The oligodeoxynucleotide primers are added to a final concentration of 0.2 to about 10 μM each and most preferably at about 1.0 μM each. (3) The RNA-dependent DNA polymerase is added to a final concentration of about 2 U/μl to about 10 U/μl, and preferably at 4 U/μl. (4) The DNA-dependent RNA polymerase is added at about 2 U/μl to about 25 U/μl, and preferably at about 5 U/μl. (5) The cell-free in vitro translation composition is added at about 50% volume:volume. Additional components of the system of the invention can be added, but are not required for the use of the invention. These include: (1) potassium acetate from about 0 to about 100 mM, preferably 3 mM; (2) spermidine from about 0 to about 0.5 mM, preferably, 0.2 mM; and (3) dithiothreitol from about 0 to about 10 mM and preferably at 5 mM.

The following examples are intended to illustrate but not limit the invention. While they are typical of those that might be used, other procedures known to those skilled in the art may alternatively be used.

EXAMPLE 1

Determination of Optimal Conditions for Coupled in vitro Polynucleotide Amplification and Translation The present invention provides a cell-free system for polynucleotide amplification and in vitro translation that produces large quantities of protein according to the protocol outlined below. Modifications are anticipated as outlined in the Detailed Description of the invention.

The coupled reaction system is highly sensitive to $MgCl_2$ concentration. FIG. 1 shows isothermal amplification of RNA in the presence of varying concentrations of $MgCl_2$. Reaction conditions were as described below for the coupled system with the exception that $MgCl_2$ concentrations were varied. The only radiolabeled substance for following RNA synthesis was $[\alpha-^{32}P]$-GTP in this experiment; $^{35}$S-methionine was not included. The marker lane (M) shows the control, with transcription products obtained at 10 mM $MgCl_2$ in the absence of amino acids and reticulocyte lysate. Reaction products were separated on a 5% polyacrylamide/ 8M urea gel. Isothermal RNA amplification proceeded within the range of 7.5–10.0 mM $MgCl_2$ as seen by the incorporation of $[\alpha-^{32}P]$-GTP into newly synthesized RNA (FIG. 1).

Reaction Conditions 1 nM L-21 RNA (5'-truncated form of self-splicing group I intron from *Tetrahymena thermophila*) (US Biochemical Co., Cleveland, Ohio)

1.0 μM (each) oligodeoxynucleotide primers 0.2 mM (each) dNTPs (dATP, dCTP, dGTP, dTTP)

2.4 mM (each) rNTPs (ATP,CTP,GTP,UTP)

$[\alpha-^{32}P]$-GTP at 0.3 mCi/ml (optional to monitor RNA synthesis)

Amino acid mixture minus methionine (Promega)

$^{35}$S-methionine, 1000 Ci/mmol (Amersham) at 0.8 mCi/ml (optional to monitor protein synthesis)

7.5 mM $MgCl_2$ 40 mM Tris-HCl, pH 7.5

Promega TNT™ rabbit reticulocyte lysate, 50% v/v (Promega, Madison, Wis.)

4 U/μl MoMLV RT

5 U/μl T7 RNA polymerase

The tube was vortexed lightly and incubated for 2 hours at 37° C. After 2 hours, the reaction was stopped by the addition of EDTA (10 mM final) to the tube. TE buffer was added to bring the volume to a total of 50 μl. The reaction tube was phenol extracted followed by $CHCl_3$:isoamyl alcohol extraction. The aqueous layer containing the reaction products was analyzed by polyacrylamide gel electrophoresis (PAGE) using methods well known in the art.

The oligodeoxynucleotide primers were as follows:

| Primer 1: | 5'-CGA | GTA | CTC | CAA | AAC | TAA | TC-3' | | | |
|---|---|---|---|---|---|---|---|---|---|---|
| Primer 2: | 5'-CTG | CAG | AAT | TCT | AAT | ACG | ACT | CAC | TAT | AGG AGG |
| | GAA | AAG | TTA | TCA | GGC-3' | | | | | |

Primer 1 is a 20-mer that binds to the 3'-terminal region of the mRNA, 10–50 nucleotides downstream from the stop codon, with a desired Tm for binding of about greater than or equal to 50° C. Primer 2 is a 48-mer that binds to the extreme 3' end of the cDNA that results from reverse transcription of the mRNA. It also binds with a Tm of about greater than or equal to 50° C. Each primer forms 12–20 base pairs with its corresponding primer binding site. Primer 2 contains 5 nucleotides, an Eco RI site, the promoter sequence for the T7 RNA polymerase, and 19 additional nucleotides.

Figure 2:
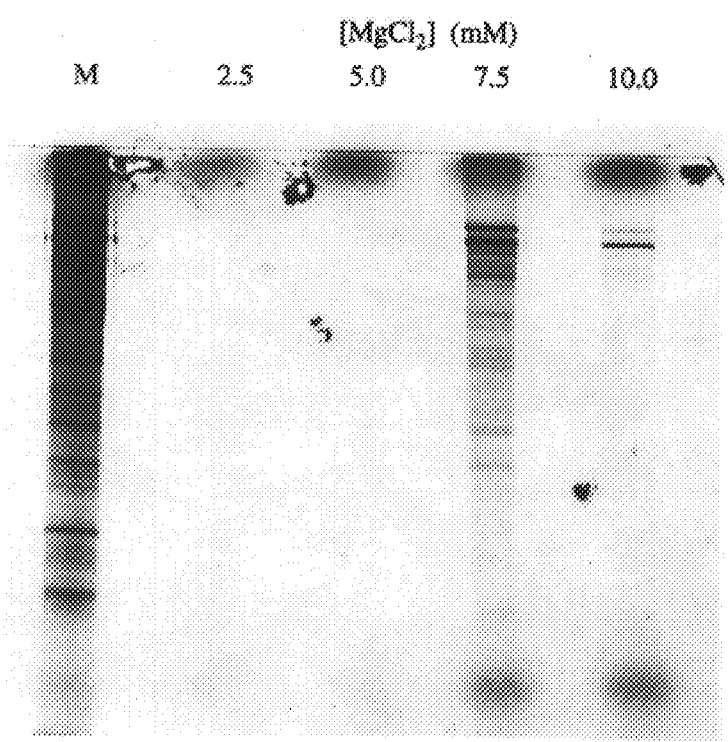
FIG. 2 shows in vitro translation of RNA in the presence of varying concentrations of $MgCl_2$, in the coupled system. $^{35}$S-methionine was included to show incorporation into protein.

In vitro translation proceeded under the same set of reaction conditions, as shown by the incorporation of $^{35}$S-methionine into newly synthesized protein. FIG. 2 shows in vitro translation of RNA in the presence of varying concentrations of $MgCl_2$ under reaction conditions as described above for the coupled system. Also included was 0.02 μg/μl brome mosaic virus (BMV) genomic RNA (Promega Biotec). Marker lane (M) shows the control with BMV genomic RNA translation products obtained at 0.5 mM $MgCl_2$ in the absence of NTPs, dNTPs, oligodeoxynucleotide primers, MoMLV RT and T7 RNA polymerase. Reaction products were separated on an SDS/10% polyacrylamide stacking gel.

Translation did not occur below 6.0 mM $MgCl_2$ in the coupled reaction system, even though in vitro translation alone operated efficiently at 0.5 mM $MgCl_2$ (Marker lane, M, FIG. 2). This apparent discrepancy may be due to complexation of $Mg^{2+}$ with deoxyribo- and ribonucleoside triphosphates that are present in the coupled reaction system. Such complexation could substantially reduce the available amount of $Mg^{2+}$.

EXAMPLE 2

Coupled Isothermal RNA Amplification and in vitro Translation

The following were added in a single microfuge tube under the stated reaction conditions:
1 nM L-21 RNA (5'-truncated form of self-splicing group I intron from *Tetrahymena thermophifa*) (US Biochemical Co., Cleveland, Ohio)
1.0 µM (each) deoxyoligonucleotide primers
0.2 mM (each) dNTPs (dATP, dCTP, dGTP, dTTP)
2.4 mM (each) rNTPs (ATP,CTP,GTP,UTP)
0.02 µg/µl BMV genomic RNA
[α-$^{32}$P]-GTP at 0.3 mCi/ml (optional to monitor RNA synthesis)
Amino acid mixture minus methionine (Promega)
$^{35}$S-methione, 1000 Ci/mmol (Amersham) at 0.8 mCi/ml (optional to monitor protein synthesis)
7.5 mM $MgCl_2$
40 mM Tris-HCl, pH 7.5
Promega TNT™ rabbit reticulocyte lysate, 50% v/v (Promega, Madison, Wis.)

The enzymes (RT and RNA polymerase) were added at 4 U/µl MOMLV RT and 5 U/µl T7 RNA polymerase. The tube was vortexed lightly and incubated for 2 hours at 37° C. After 2 hours, the reaction was stopped by the addition of EDTA (10 mM final) to the tube. TE buffer was added to bring the volume to a total of 50 µl. The reaction tube was phenol extracted followed by $CHCl_3$:isoamyl alcohol extraction. The aqueous layer containing the reaction products was analyzed by polyacrylamide gel electrophoresis (PAGE) using methods well known in the art. The results showed that isothermal amplification of RNA and in vitro translation proceeded under the same set of reaction conditions in the same tube.

The invention now being fully described, it will be apparent to one of ordinary skill in the art that various changes and modifications can be made without departing from the spirit or scope of the invention.

I claim:

1. A cell-free system for amplification and translation of prokaryotic polynucleotide sequences comprising:
    reverse transcriptase, polynucleotide primer which allows the reverse transcriptase to function, DNA-dependent RNA polymerase, polynucleotide primer which allows the DNA-dependent RNA polymerase to function, deoxyribonucleotide triphosphate, ribonucleoside triphosphate, and a cell free in vitro translation composition comprising a magnesium source in a concentration of from 6.0 to 10.0 mM,
    wherein the components of the system function under a common set of reaction conditions, and wherein DNA and RNA amplification and translation operate simultaneously.

2. The system of claim 1, wherein the reverse transcriptase is selected from the group consisting of Moloney murine leukemia virus RT and avian myeloblastosis virus RT.

3. The system of claim 1, wherein the DNA dependent RNA polymerase is derived from a bacteriophage.

4. The system of claim 3, wherein the bacteriophage is selected from the group consisting of T7, T3, and SP6 bacteriophage.

5. The system of claim 1, wherein the cell-free in vitro translation composition is derived from a eukaryotic cell.

6. The system of claim 5, wherein the eukaryotic cell is a plant cell.

7. The system of claim 6, wherein the plant cell is wheat cell.

8. The system of claim 5, wherein the eukaryotic cell is an animal cell.

9. The system of claim 8, wherein the animal cell is a reticulocyte.

10. The system of claim 9, wherein the reticulocyte is a rabbit reticulocyte.

11. A composition, comprising:
    (a) a transcription and translation enzyme compatible biological buffer;
    (b) A magnesium source in a concentration of from 6.0 to 10.0 mM;
    (c) deoxyribonucleotide triphosphate;
    (d) ribonucleoside triphosphate;
    (e) amino acids;
    (f) reverse transcriptase and polynucleotide primer which allows the reverse transcriptase to function; and
    (g) DNA-dependent RNA polymerase and polynucleotide primer which allows the DNA-dependent RNA polymerase to function.

12. The composition of claim 11, wherein the biological buffer is a tris(hydroxymethyl) aminomethane salt.

13. The composition of claim 11, wherein the magnesium source is a salt.

14. The composition of claim 13, wherein the salt is $MgCl_2$.

15. A method for producing polypeptide comprising amplifying and translating a eukaryotic polynucleotide which encodes the polypeptide using a cell-free system of claim 1.

16. The method of claim 15, wherein the polynucleotide is mRNA.

17. The method of claim 15, wherein the polynucleotide is DNA.

18. The method of claim 17, wherein the DNA is cDNA.

19. A cell-free system according to claim 1 wherein the magnesium source is $MgCl_2$.

* * * * *